United States Patent [19]

Noiles et al.

[11] Patent Number: 4,473,077
[45] Date of Patent: Sep. 25, 1984

[54] SURGICAL STAPLER APPARATUS WITH FLEXIBLE SHAFT

[75] Inventors: Douglas Noiles, New Canaan; Alfred F. DeCarlo, Stamford, both of Conn.

[73] Assignee: United States Surgical Corporation, Norwalk, Conn.

[21] Appl. No.: 383,144

[22] Filed: May 28, 1982

[51] Int. Cl.³ .............................................. A61B 17/11
[52] U.S. Cl. ................................ 128/305; 128/334 R; 227/19; 227/DIG. 1; 74/501 P
[58] Field of Search ............... 128/334 R, 334 C, 305, 128/772, 4, 5, DIG. 9; 227/19, DIG. 1; 74/501 P

[56] References Cited

U.S. PATENT DOCUMENTS

| | | | |
|---|---|---|---|
| 2,905,178 | 9/1959 | Hilzinger | 128/303 R |
| 3,452,615 | 7/1969 | Gregory | 74/501 P |
| 3,552,626 | 1/1971 | Astafiev et al. | 227/76 |
| 3,638,652 | 2/1972 | Kelley | 128/305 |
| 3,837,555 | 9/1974 | Green | 227/130 |
| 3,952,747 | 4/1976 | Kimmell, Jr. | 128/303 R |
| 4,108,211 | 8/1978 | Tanaka | 128/4 X |
| 4,319,576 | 3/1982 | Rothfuss | 128/305 |
| 4,351,466 | 9/1982 | Noiles | 227/8 |

FOREIGN PATENT DOCUMENTS

| | | |
|---|---|---|
| 2347418 | 9/1973 | Fed. Rep. of Germany . |
| 1185292 | 3/1970 | United Kingdom . |
| 2016991A | 9/1979 | United Kingdom . |
| 2038692A | 7/1980 | United Kingdom . |
| 266139 | 3/1973 | U.S.S.R. . |

Primary Examiner—Michael H. Thaler
Attorney, Agent, or Firm—John E. Nathan; Robert E. Jackson; Richard A. Inz

[57] ABSTRACT

A surgical stapler including a stapling assembly, an actuator assembly remote from the stapling assembly, and a longitudinal shaft assembly having a longitudinally flexible section for connecting the actuator assembly to the stapling assembly and for transmitting the forces and motions required to operate the stapling assembly from the actuator assembly to the stapling assembly.

21 Claims, 21 Drawing Figures

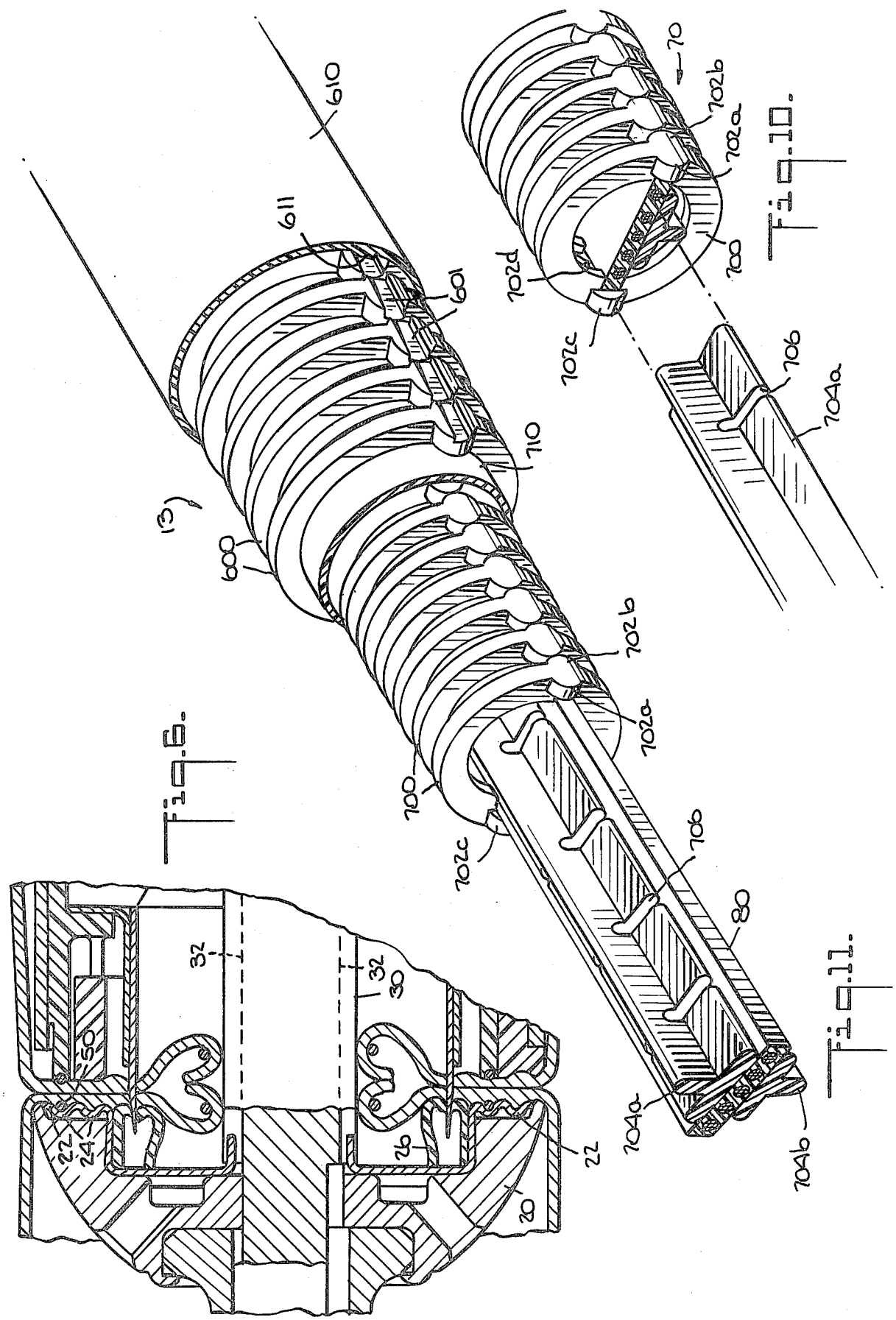

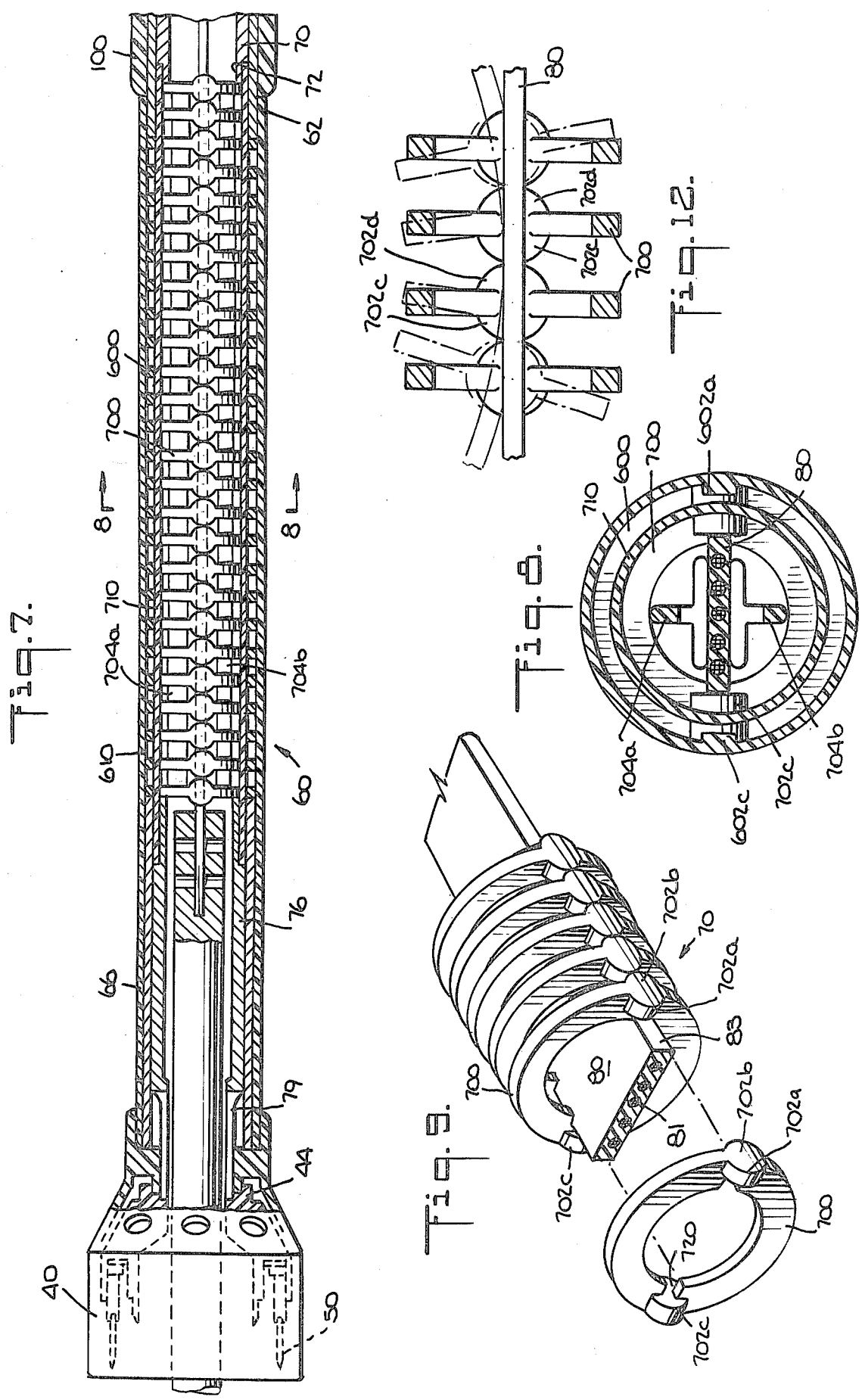

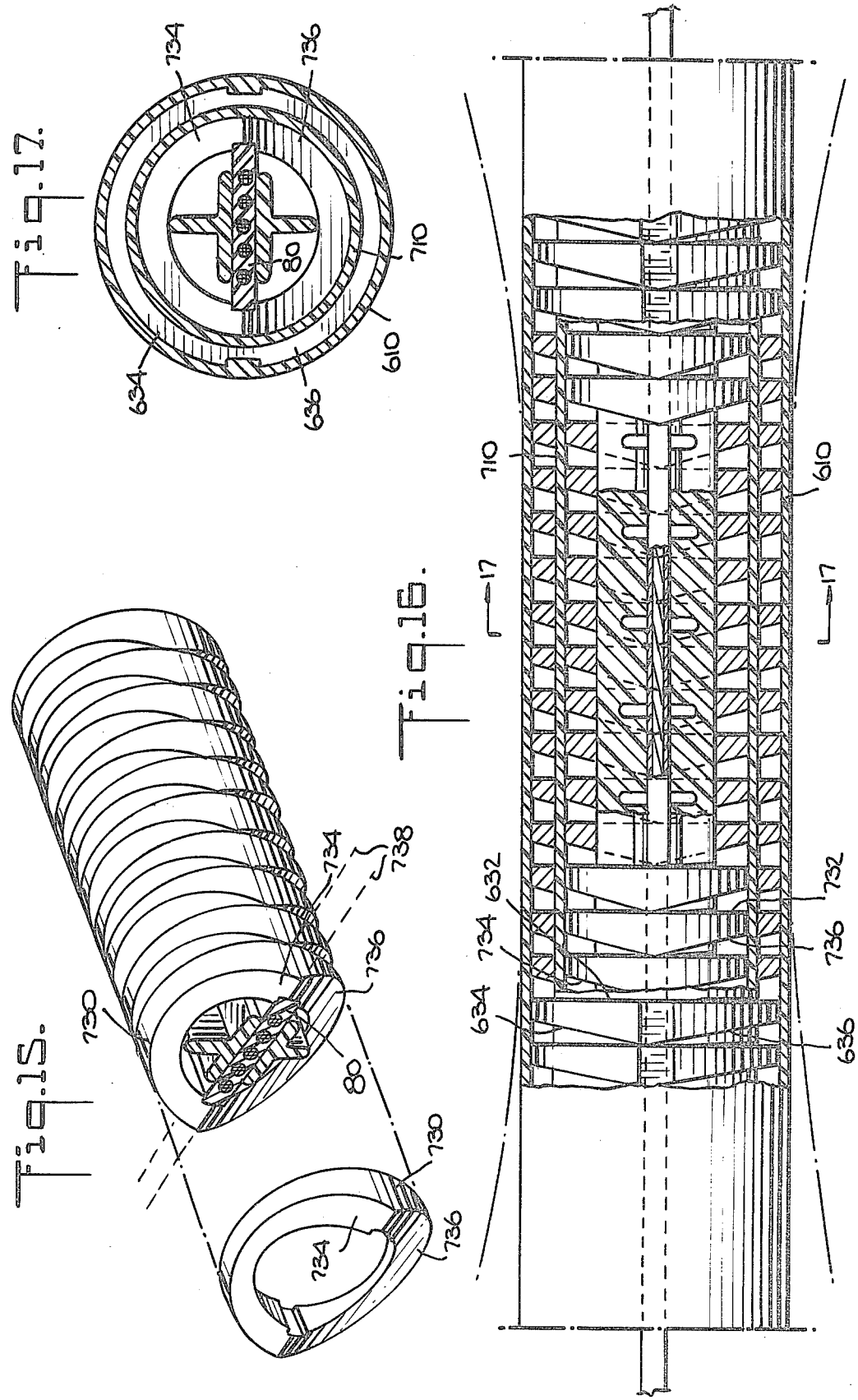

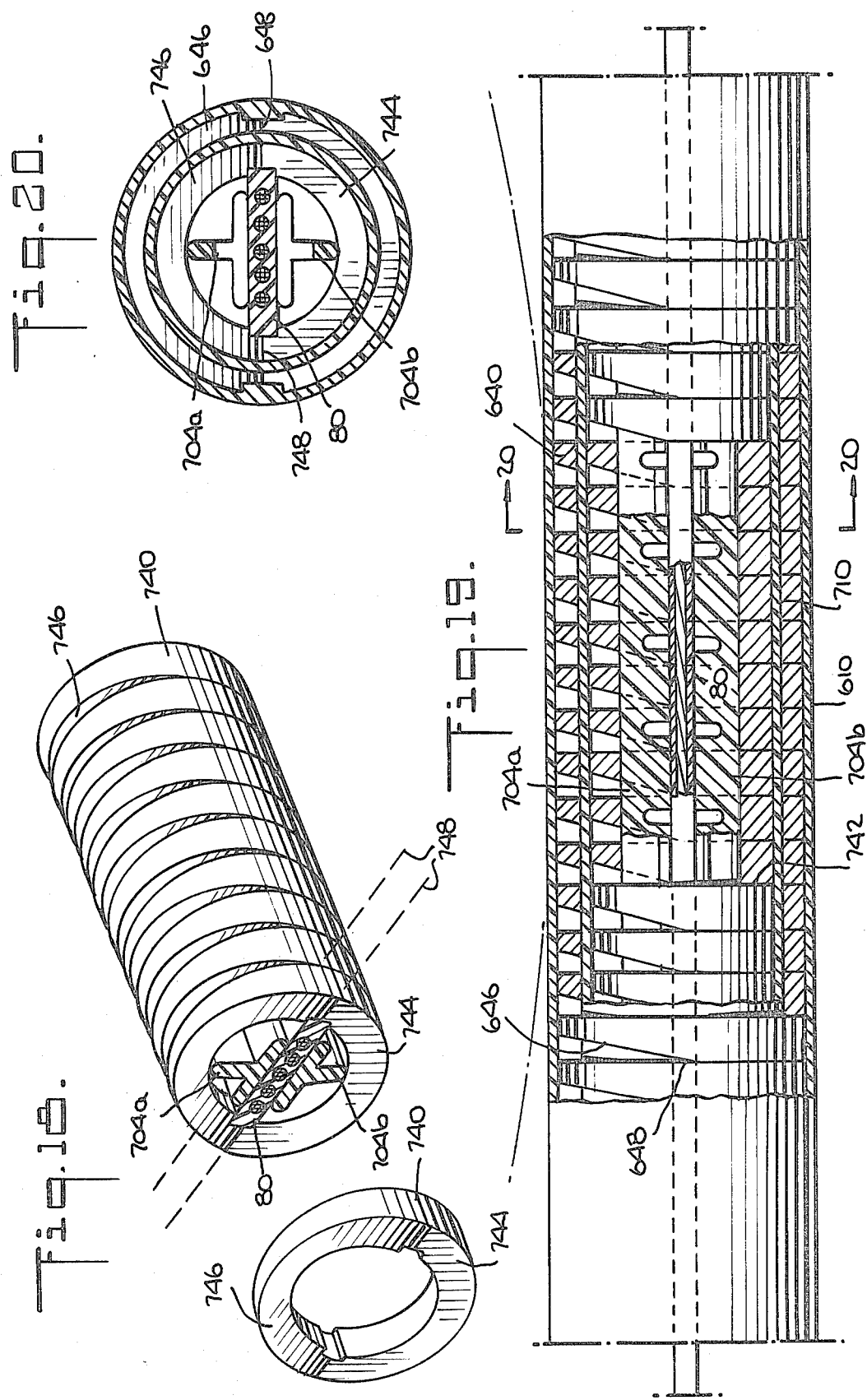

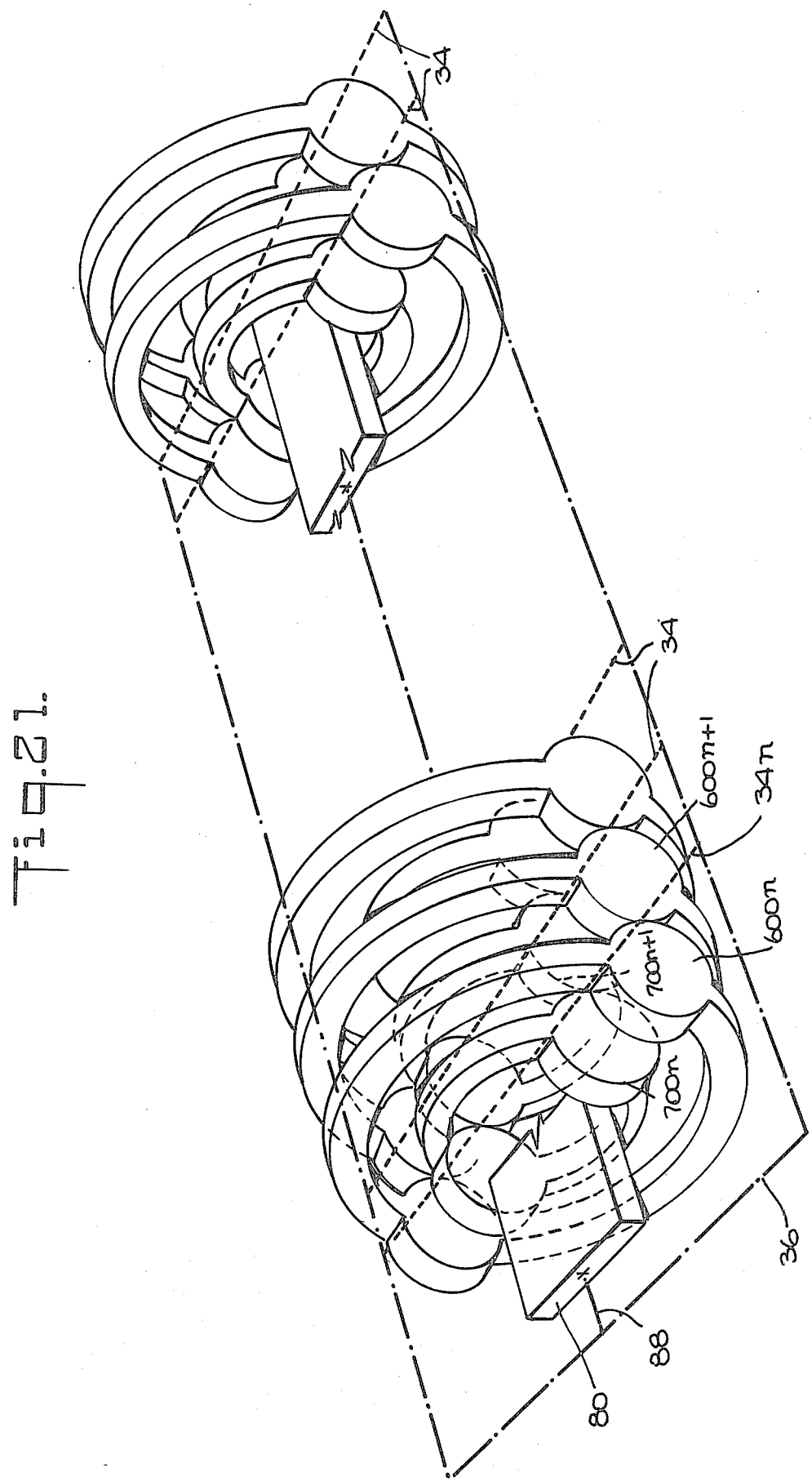

SURGICAL STAPLER APPARATUS WITH FLEXIBLE SHAFT

BACKGROUND OF THE INVENTION

This invention relates to apparatus for applying surgical staples and other surgical fasteners, and more particularly to such apparatus having a longitudinally flexible shaft intermediate the portion of the apparatus which performs the stapling function and the actuator portion of the apparatus. (For simplicity, discussion will hereinafter be confined, in terms, to surgical staplers, but it is to be understood that the scope of the invention extends to apparatus for applying any type of surgical fasteners.)

There are several known types of surgical staplers in which the stapling function takes place at a location which is relatively remote from the location at which the stapler is held and actuated by the operator. Examples of such staplers are the linear closure surgical staplers shown illustratively in Green et al. U.S. Pat. No. 3,494,533 and the circular anastomosis surgical staplers shown illustratively in Conta et al. U.S. Pat. No. 4,304,236. Typically, in instruments of the types exemplified by these patents, tissue to be stapled is clamped between an anvil assembly and a staple holding assembly, both of which are located at the distal end of the instrument. The clamped tissue is stapled by driving one or more staples from the staple holding assembly so that the ends of the staples pass through the tissue and are clinched by contact with the anvil assembly. The forces required to operate the instrument are applied by the operator of the instrument to one or more actuator elements located at or near the proximal end of the instrument. The distal and proximal portions of the instrument are joined by a longitudinal connecting shaft structure along which the actuating forces and motions are transmitted to the distal operating elements. This type of construction, including relatively widely spaced distal and proximal portions, may be employed for any of several reasons, such as the relative inaccessibility of the tissue to be stapled, the need for good visibility of the tissue during stapling, and the like.

In some applications of instruments of the types mentioned above it may be desirable for the longitudinal shaft structure joining the distal and proximal portions of the apparatus to have at least a section which is longitudinally flexible. This may facilitate placement of the instrument in particular body structures, it may facilitate reaching remote or relatively inaccessible stapling sites, or it may allow the staples to be presented at the stapling site at various angles relative to the operator of the instrument. However, this type of instrument construction means that the actuating forces and motions must be transmitted through a flexible structure capable of taking on a variety of curvatures. This considerably complicates the design of the instrument. In addition to transmitting actuating forces and motions through a variety of curvatures, the structure must generally transmit these forces and motions without significant straightening, and without significantly greater frictional losses than would be present in a comparable straight instrument. Both the control of the tendency to straighten and the control of friction losses are much more difficult in a flexible instrument than in a comparable rigid instrument.

In view of the foregoing, it is an object of this invention to provide improved surgical staplers having a flexible shaft structure between the distal stapling elements and the proximal actuating elements.

SUMMARY OF THE INVENTION

This and other objects of the invention are accomplished in accordance with the principles of the invention by providing surgical stapling apparatus including a flexible shaft assembly which can be deformed into a curve and which will maintain that curve while transmitting forces between an actuator assembly and a remote stapling assembly. The shaft assembly includes a longitudinally flexible compression member for transmitting longitudinal compression forces with the compression forces producing a resultant force normal to the longitudinal axis of the flexible shaft assembly when the assembly is curved, a longitudinally flexible tension member for transmitting longitudinal tension forces with the tension forces producing a resultant force which is normal to the longitudinal axis of the flexible shaft assembly when the assembly is curved and which is essentially equal in magnitude and opposite in direction to the resultant force produced by the compression member when the tension and compression forces are equal, and means for transmitting resultant forces between the compression member and the tension member while allowing relative longitudinal motion between those members. By linking and matching the resultant forces produced by the compression member and the tension member through the means for transmitting resultant forces, the overall assembly is essentially in equilibrium in the direction normal to its longitudinal axis. This greatly reduces or essentially eliminates the tendency of the shaft assembly to revert to its straight condition during the transmittal of longitudinal forces.

Further features of the invention, its nature and various advantages will be more apparent from the accompanying drawing and the following detailed description of the invention.

BRIEF DESCRIPTION OF THE DRAWING

FIGS. 2 and 3 connect to one another along the left in FIG. 2 and the right in FIG. 3 and show the same condition of the apparatus.

FIG. 6 is an enlarged longitudinal sectional view of a portion of the apparatus of FIGS. 1-5 showing the tissue after it has been stapled and cut by the apparatus.

FIGS. 7 through 14 illustrate a first embodiment of the invention wherein disc-shaped segments having cylindrically-shaped projections provide flexibility for the shaft assembly.

FIG. 7 is a longitudinal sectional view showing the shaft assembly in its undeformed condition.

FIG. 8 is a transverse sectional view along line 8—8 in FIG. 7 showing the radial organization of the various components of the flexible shaft assembly.

FIGS. 9–11 are perspective views showing the shaft assembly in various stages of partial disassembly.

FIG. 12 is a schematic drawing illustrating the motions of adjacent segments as the shaft assembly is deformed into a curve.

FIGS. 13 and 14 are longitudinal sectional views showing the shaft assembly in its straight and curved conditions, respectively.

FIGS. 15–17 illustrate an alternate embodiment of the invention wherein flexibility of the shaft assembly is provided by segments having a flat rear surface and a front surface having two bevelled portions.

FIG. 15 is a perspective view of the shaft assembly partially disassembled.

FIG. 16 is a longitudinal sectional view showing the shaft assembly in its undeformed condition and illustrating, in phantom, deformation of the shaft above and below the median plane of the instrument.

FIG. 17 is a transverse sectional view along line 17—17 in FIG. 16 showing the radial organization of the various components of the shaft assembly.

FIGS. 18–20 illustrate a second alternate embodiment of the invention wherein flexibility of the shaft assembly is provided by segments having a flat rear surface and a front surface having a flat portion and a bevelled portion.

FIG. 18 is a perspective view of the shaft assembly partially disassembled.

FIG. 19 is a longitudinal sectional view showing the shaft assembly in its undeformed condition and illustrating, in phantom, deformation of the shaft above the median plane of the instrument.

FIG. 20 is a transverse sectional view along line 20—20 in FIG. 19 showing the radial organization of the various components of the shaft assembly.

FIG. 21 is a schematic diagram illustrating the spatial relationships between the tension and compression members of the flexible shaft assembly.

DETAILED DESCRIPTION OF THE INVENTION

Although the invention is applicable to other types of surgical staplers, as mentioned above, the invention will be fully understood from an explanation of its application to a particular circular anastomosis surgical stapler embodiment.

Figure 1:
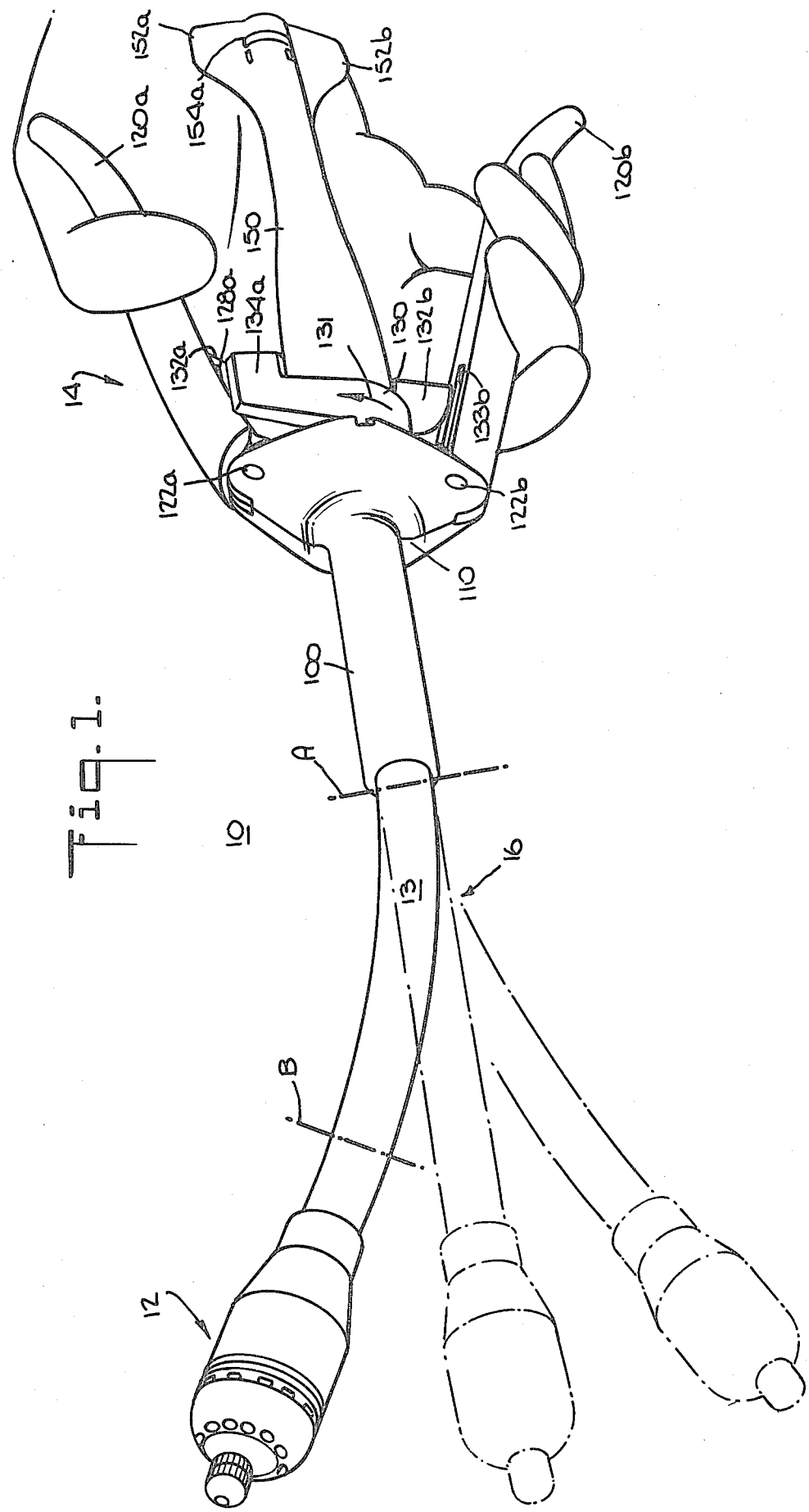
FIG. 1 is a perspective view of a surgical stapler constructed in accordance with this invention.

An illustrative embodiment of the invention is the circular anastomosis surgical stapler 10 shown generally in FIG. 1. A typical application of stapler 10 is connecting two sections of hollow tubular body organ (e.g., two intestinal sections) by means of an annular array of staples surrounding a lumen or passageway of the organ. Stapler 10 includes distal stapling assembly 12, proximal actuator assembly 14, and longitudinal shaft assembly 16 for connecting the distal and proximal assemblies and for transmitting actuating forces and motions from the actuator assembly to the stapling assembly.

In accordance with the present invention, shaft assembly 16 has a longitudinally flexible portion 13 extending from section A to section B. In the particular embodiment shown in FIG. 1, this portion can be flexed both above and below the median plane of the instrument. In an alternate embodiment described below, the instrument can only be flexed in one direction from the median plane. Although the maximum deviation from the straight condition and the radius of curvature through the flexible portion corresponding to that deviation may depend on the type and intended application of the instrument, in a typical instrument intended for joining intestinal sections, the maximum deviation may be about 30° and the radius of curvature corresponding to that deviation may be about 6 inches.

Figure 3:
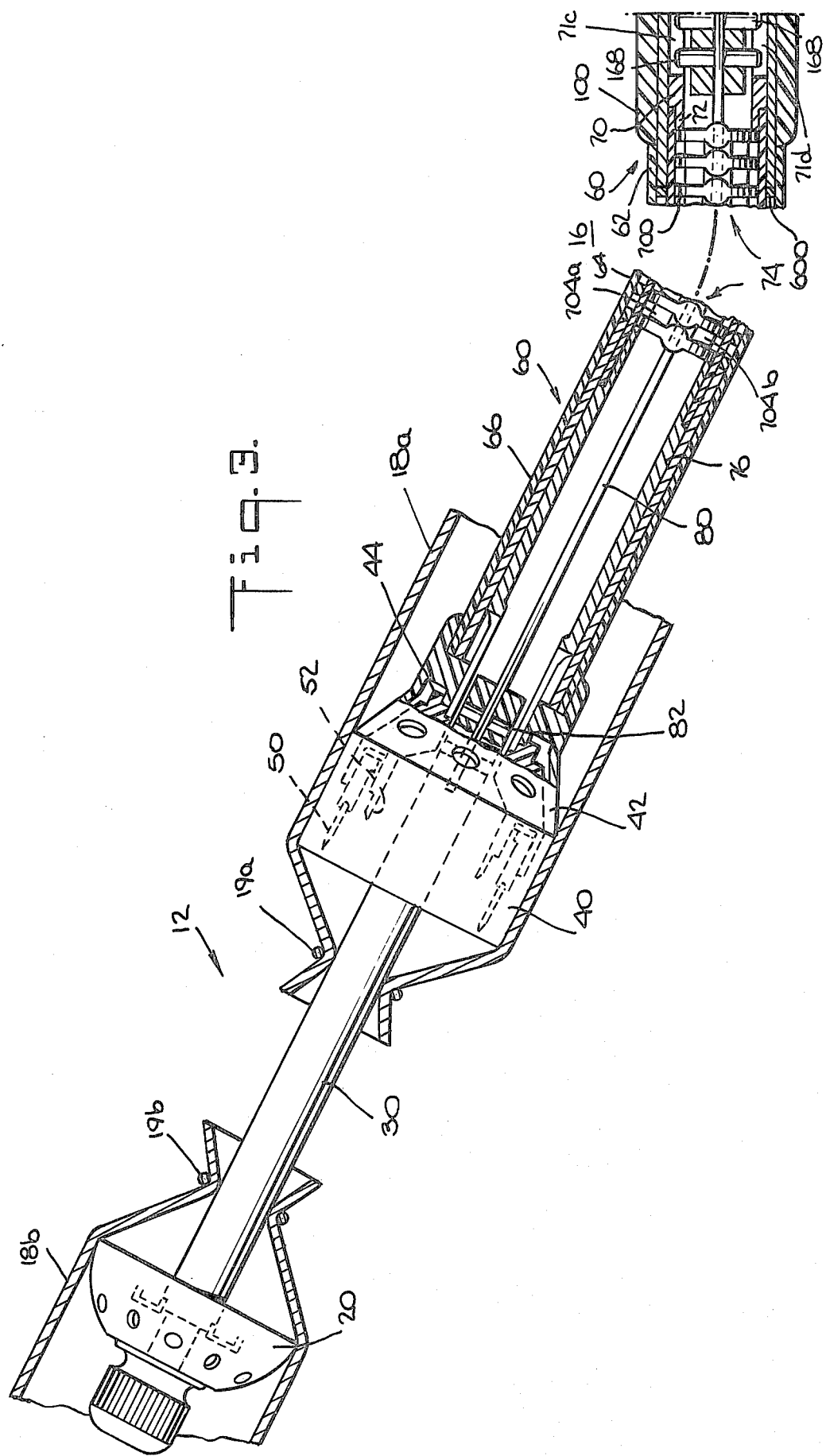
FIG. 3 is a fragmented longitudinal sectional view of the portion of the apparatus of FIG. 1 which is not shown in FIG. 2.

Stapling assembly 12, which is best described initially with reference to FIG. 3, includes anvil assembly 20 mounted on the distal end of anvil support rod 30 and staple holding assembly 40. Rod 30 is mounted for longitudinal reciprocal motion relative to staple holding assembly 40 so that the spacing between the opposing faces of assemblies 20 and 40 can be varied. As can be seen in FIG. 6, anvil assembly 20 includes annular staple anvil 22 and annular cutting ring 26. Returning to FIG. 3, staple holding assembly 40 includes a housing 42 which initially holds a plurality of U-shaped metal surgical staples 50 arranged in two closely spaced concentric annular rows. The sharply pointed free ends of the legs of each staple 50 point in the distal direction toward anvil assembly 20. Staple holding assembly 40 also contains annular tissue cutting knife 52 concentric with and inside the annular array of staples 50. The sharpened tissue cutting edge of knife 52 points in the distal direction toward cutting ring 26 of anvil assembly 20. Also included in staple holding assembly 40 is a pusher assembly 44 mounted for longitudinal motion relative to housing 42 for driving staples 50 and knife 52 toward anvil assembly 20.

Anvil assembly 20 and staple holding assembly 40 are both keyed to rod 30 so that anvil assembly 20 cannot rotate relative to staple holding assembly 40 about the longitudinal axis of the apparatus. This keeps staples 50 aligned with staple clinching grooves or pockets 24 (FIG. 6) in staple anvil 22, as is necessary for proper clinching of the staples by the anvil.

While not necessary to an understanding of the present invention, additional details regarding the construction of stapling assemblies of the type described above may be found in the above-mentioned Conta et al. U.S. Pat. No. 4,304,236.

Figure 5:
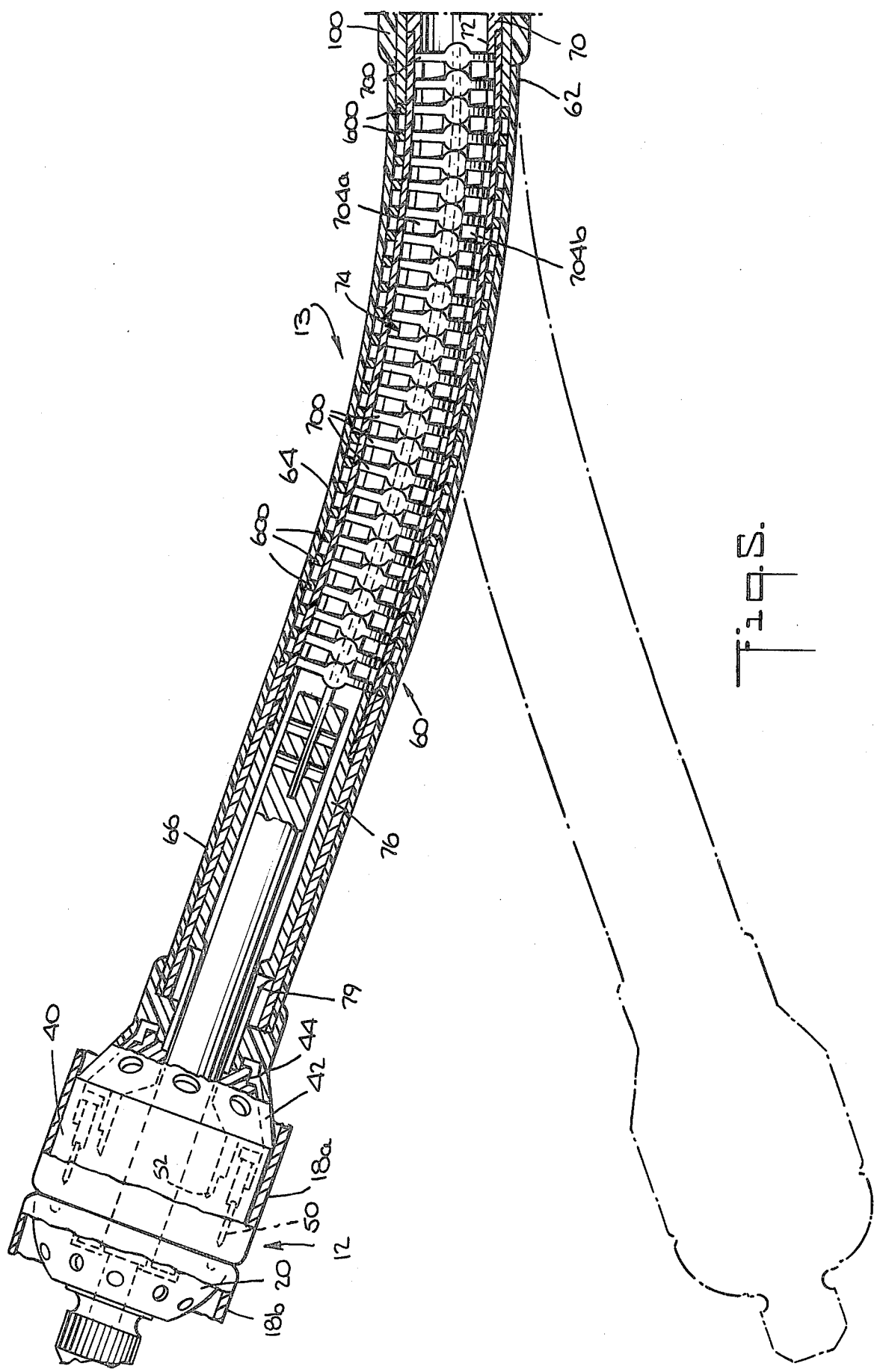
FIG. 5 is similar to FIG. 3, but shows the elements of the apparatus in the condition corresponding to the actuator condition shown in FIG. 4.

In use in the typical application of joining two intestinal sections together, the flexible portion 13 of shaft assembly 16 is first deformed into a curve appropriate for the particlar patient and for the surgical operation being performed. Then the instrument is positioned relative to the tissue, as shown in FIG. 3, so that staple holding assembly 40 is inside the end of one intestinal section 18a and anvil assembly 20 is inside the end of the other intestinal section 18b. The severed ends of organ sections 18a and 18b are secured around rod 30 between assemblies 20 and 40 by means of manually applied pursestring sutures 19a an 19b, respectively. The instrument is then operated as described below to retract anvil supporting rod 30 and thereby draw anvil assembly 20 toward staple holding assembly 40. When anvil supporting rod 30 is fully retracted as shown in FIG. 5, organ sections 18a and 18b are firmly clamped together between the opposing faces of anvil assembly 20 and staple holding assembly 40.

When the tissue of the organ sections has been clamped together as described above, the instrument is further operated as described below to drive the annular array of staples 50 from staple holding assembly 40, through the clamped tissue, and against staple anvil 22 as shown in FIG. 6. Staple anvil 22 clinches the ends of staples 50 so that the two organ sections are securely fastened together by the annular array of staples. The same operation of the instrument which drives the staples also drives knife 52 to cut away the waste or excess tissue inside the annular array of staples, thereby clearing the lumen between the connected organ sections. The joining of the organ sections is now complete and the instrument can be removed as described below.

To remove the instrument from the stapled tissue, anvil assembly 20 is again separated from staple holding assembly 40 so that the tissue is no longer clamped by the instrument. The instrument is then withdrawn by pulling it out through organ section 18a. The excess tissue cut away by knife 52 remains secured to rod 30 by sutures 19a and 19b so that this tissue is removed with the instrument.

Actuator assembly 14 allows the operator of the instrument to produce the above-described operations of stapling assembly 12. Shaft assembly 16 transmits the required forces and motions from actuator assembly 14 to stapling assembly 12.

As can be seen for example in FIGS. 3 and 5, shaft assembly 16 includes a hollow outer tube assembly 60. As discussed in detail below, tube assembly 60 serves as a compression member for transmitting a longitudinal compression force from actuator assembly 14 to staple holding assembly 40 during clamping of organ sections 18a and 18b between anvil assembly 20 and staple holding assembly 40. By transmitting this compression force, tube assembly 60 holds staple holding assembly 40 essentially stationary with respect to actuator assembly 14 as anvil assembly 20 is pulled tight against staple holding assembly 40.

Tube assembly 60 includes a straight proximal portion 62, a flexible intermediate portion 64 and a straight distal portion 66. Secured to proximal portion 62 is main body 100 of actuator assembly 14. Mounted on distal portion 66 is housing 42 of staple holding assembly 40. Between portions 62 and 66 is flexible portion 64, composed of segments or elements 600. These segments 600 allow tube assembly 60 to be bent into a curve and to maintain that curve while transmitting compression force. The construction and operation of segments 600 are discussed below.

Figure 2:
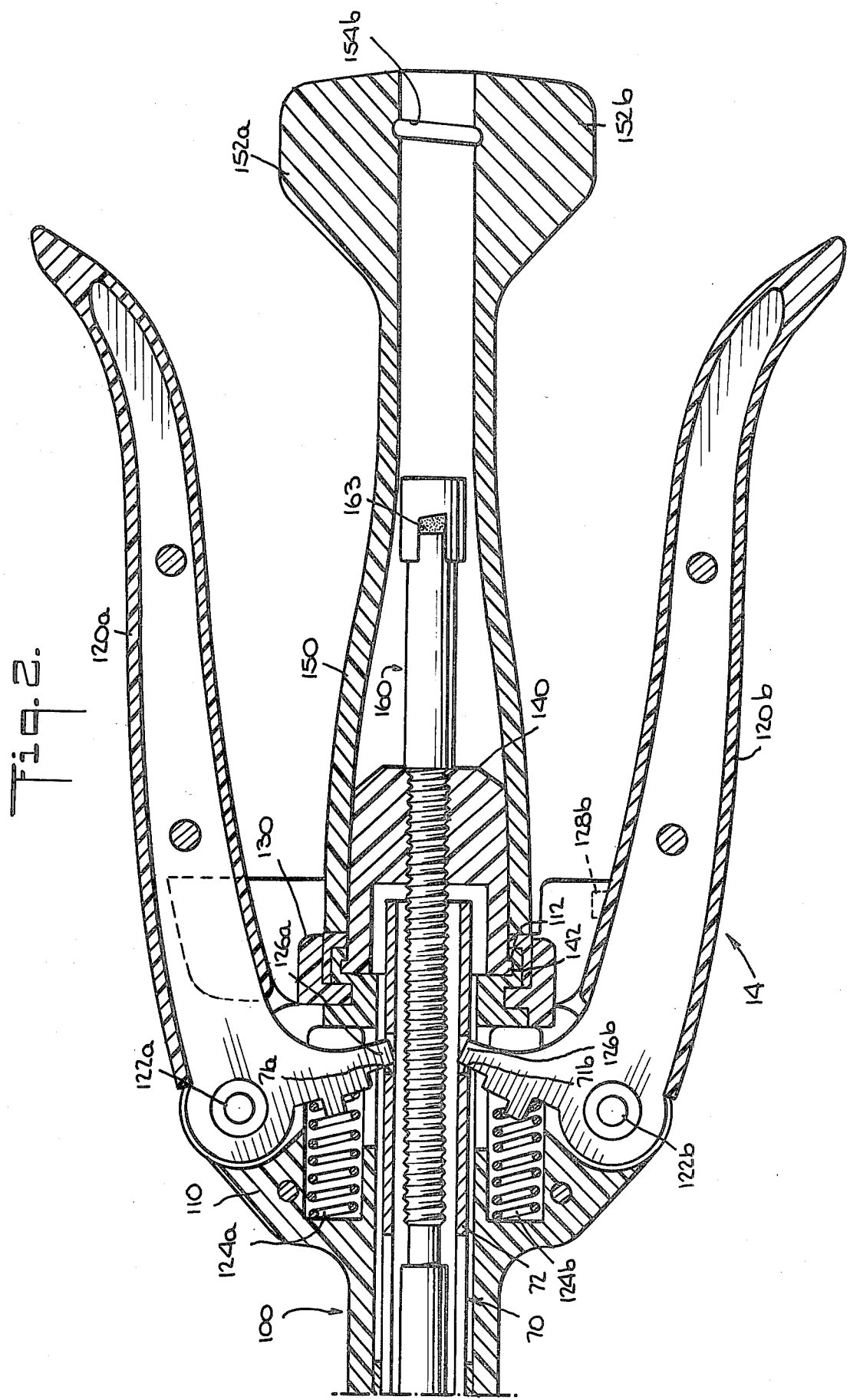
FIG. 2 is a longitudinal sectional view of the actuator portion of the apparatus of FIG. 1 showing that apparatus in the condition which produces the maximum separation between the anvil assembly and the staple holding assembly.

As is best seen in FIGS. 1 and 2, actuator body 100 includes a proximal yoke 110 on which proximally extending opposing handles 120a and 120b are pivotally mounted by means of pins 122a and 122b, respectively. Handles 120a and 120b are resiliently biased outward by compression coil springs 124a and 124b (FIG. 2) inside yoke 110. As is described in detail below, staples 50 and knife 52 are driven by squeezing handles 120a and 120b together.

To prevent accidental premature squeezing of handles 120a and 120b, safety collar 130 is rotatably mounted on actuator body 100 on the proximal side of pivot pins 122a and 122b. Safety collar 130 includes wings 132a and 132b which project outward underneath handles 120a and 120b, respectively. Safety collar 130 is resiliently biased to rotate in the direction opposite the direction indicated by the arrow 131 in FIG. 1 by springs (not shown) acting between actuator body 100 and collar 130. Safety collar 130 is prevented from rotating farther in this direction than shown in FIG. 1 by inwardly extending lugs 128a and 128b on handles 120a and 120b, respectively. In this position the outer ends of wings 132a and 132b contact the undersides of handles 120a and 120b and prevent the handles from being accidentally squeezed together. Also projecting outward from safety collar 130 are identical tabs 134a and 134b (only tab 134a being visible in the drawing). Each of tabs 134a and 134b is substantially parallel to but spaced from a respective one of wings 132a and 132b on the same side of the wing as the associated lug 128a or 128b. Each tab 134a and 134b extends radially outward farther than wings 132a and 132b so that the ends of tabs 134a and 134b will contact the sides of handles 120a and 120b to stop rotation of safety collar 130 in the direction indicated by arrow 131. When it is desired to release handles 120a and 120b from contact with wings 132a and 132b, either of tabs 134a and 134b is pressed toward the adjacent handle 120a or 120b to rotate safety collar 130 in the direction of arrow 131. When the ends of tabs 134a and 134b contact the sides of handles 120a and 120b, the ends of wings 132a and 132b are respectively aligned with slots 133a and 133b in handles 120a and 120b. Wings 132a and 132b fit into slots 133a and 133b so that handles 120a and 120b can be squeezed together.

On the proximal side of yoke 110 cylindrical nut 140 (see FIG. 2) is mounted for rotation about the longitudinal axis of the instrument by means of annular flange 142 on nut 140 in cooperation with annular channel 112 in body 100. Nut cover 150 is fixedly mounted on nut 140 and extends in the proximal direction between handles 120a and 120b. The proximal end of cover 150 includes laterally extending wings 152a and 152b for facilitating rotation of cover 150 by the operator. Accordingly, nut 140 and cover 150 collectively comprise a wing nut which will be referred to hereinafter as wing nut 150. The proximal end of wing nut 150 also includes two opposite apertures 154a and 154b to allow the operator of the instrument to observe indicator marks 163 inside wing nut 150 as described below.

Inside hollow outer tube assembly 60 and actuator body 100 is hollow inner tube assembly 70 which is mounted for longitudinal motion relative to outer tube assembly 60. Tube assembly 70 includes a straight proximal portion 72 which extends from the interior of nut 140 to approximately section A, an intermediate flexible portion 74 that extends from approximately section A to approximately section B and is longitudinally aligned with intermediate portion 64 of outer tube assembly 60, and a straight distal portion 76 that extends from approximately section B into staple holding assembly 40. As discussed below, proximal portion 72 is directly connected to handles 120a and 120b, and distal portion 76 extends into staple holding assembly 40 and is in direct contact with staple and knife pusher assembly 44. In operation, tube assembly 70 constitutes a compression member for transmitting a longitudinal compression force (and an associated longitudinal motion) produced by operation of handles 120a and 120b from actuator assembly 14 to staple and knife pusher assembly 44 in staple holding assembly 40. Tube assembly 70 therefore transmits from actuator assembly 14 to stapling assembly 12 the force and motion necessary to drive staples 50 and knife 52.

During actuation, tube assembly 70 is driven in the distal direction by handle projections 126a and 126b that respectively engage apertures 71a and 71b in the sides of proximal portion 72 of the tube assembly. Thus when safety collar 130 is rotated to release handles 120a and 120b and these handles are squeezed together to the positions shown in broken lines in FIG. 4, inner tube assembly 70 moves distally relative to outer tube assembly 60 and through the contact of distal portion 76 with pusher assembly 44 drives staples 50 and knife 52 as shown in FIG. 6. The distal portion 76 contains longitudinal slots 79 (FIG. 5) for allowing keys (not shown) to extend from housing 42 into longitudinal keyways 32 (FIG. 6) in rod 30 without inhibiting the longitudinal motion of tube assembly 70. These keys cooperate with rod 30 to maintain the angular alignment of staple holding assembly 40 relative to anvil assembly 20.

Intermediate portion 74 of inner tube assembly 70, like intermediate portion 64 of outer tube assembly 60, consists of a plurality of segments or elements 700 which allow tube assembly 70 to be deformed into a curve and to maintain that curve while transmitting compression force. The details of the construction and operation of segments 700, and their relation to segments 600 of outer tube assembly 60, are discussed below.

Figure 4:
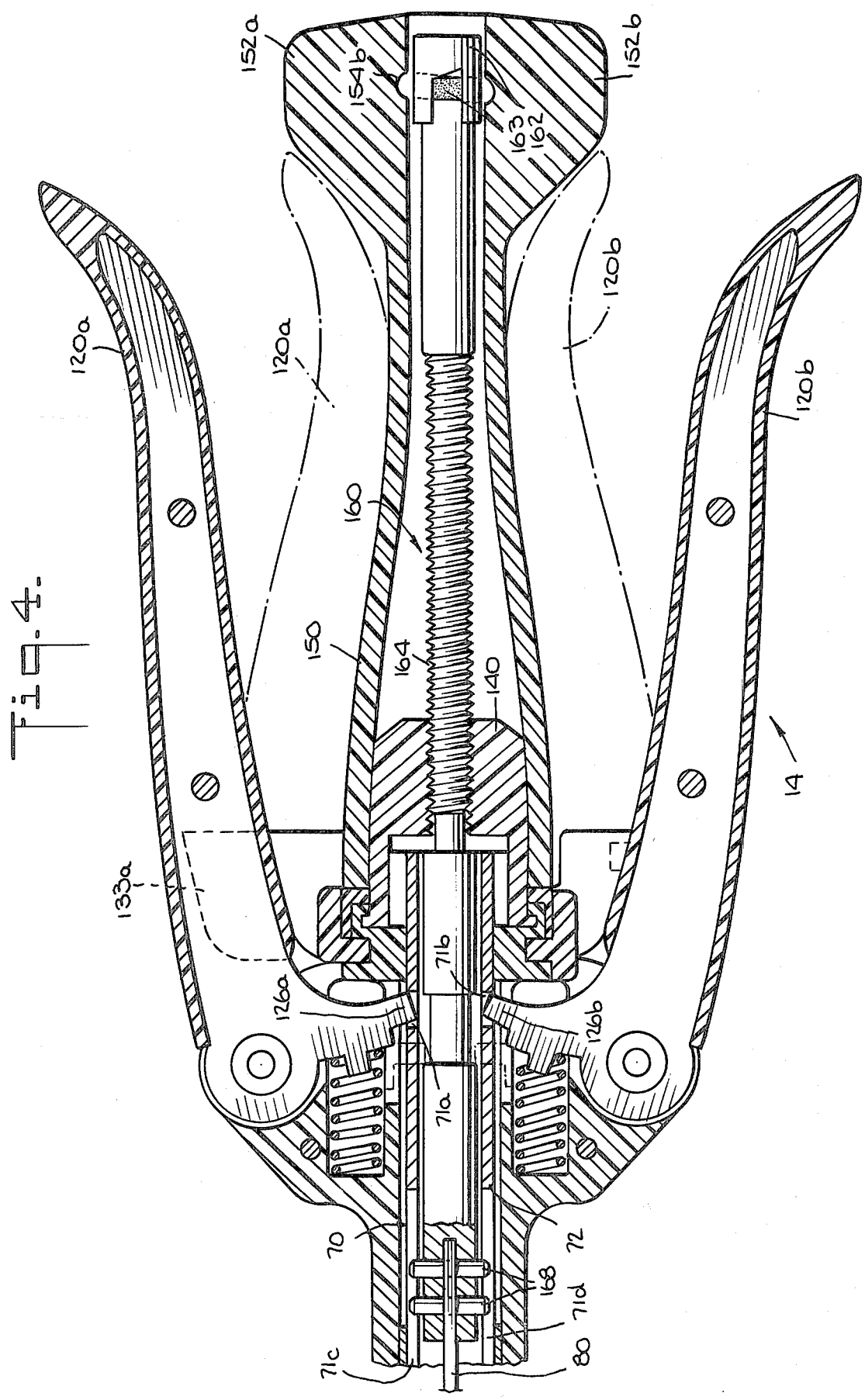
FIG. 4 is similar to FIG. 2, but shows the actuator portion of the apparatus in the condition in which the staples are driven.

Inside the proximal portion 72 of tube assembly 70 is a rod 160 (see FIGS. 2 and 4) which extends from a point on the proximal side of section A, through nut 140, and into the interior of wing nut 150. Rod 160 is mounted for longitudinal reciprocal motion relative to the surrounding elements and is prevented from rotating about its longitudinal axis by transverse pins 168 which extend through rod 160 into longitudinal slots 71c and 71d in tube assembly section 72. An intermediate section 164 of rod 160 threadedly engages nut 140 so that when wing nut 150 is rotated, rod 160 moves in the proximal or distal direction, depending on the direction of rotation of wing nut 150. The proximal end portion 162 of rod 160 includes indicator marks 163 on opposite sides of the rod. When anvil assembly 20 is sufficiently close to staple holding assembly 40 that staples 50 will be properly clinched by the anvil, indicator marks 163 are visible through apertures 154a and 154b in wing nut 150 as shown in FIG. 4.

The linear translation of rod 160 in response to rotation of wing nut 150 is transmitted to rod 30 by flexible band 80, which is mounted in tube assembly 70 for longitudinal reciprocal motion relative to the surrounding elements. Band 80 is typically made up of several small-diameter, flexible metal cables 81 embedded in a sheath 83 made of flexible plastic or a similar material. This arrangement gives the band high longitudinal flexibility and high tensile strength. The proximal end of flexible band 80 is connected to the distal end of rod 160 by pins 168, and the distal end of band 80 is connected to the proximal end of rod 30 by pins 82.

Although flexible band 80 may occasionally be required to transmit minor longitudinal compression forces (e.g., to move anvil assembly 20 away from staple holding assembly 40), the principal function of flexible band 80 is to act as a tension member for transmitting longitudinal tension force (and accompanying motion) from actuator assembly 14 to stapling assembly 12 for drawing anvil assembly 20 toward staple holding assembly 40 and then holding these two assemblies together to clamp the tissue during stapling and cutting. Because the force required to clamp the tissue may be approximately 50–100 pounds, the force required to drive the staples may be approximately 200 pounds, and the force required to drive the knife may be approximately 175 pounds, it will be apparent that flexible band 80 may be required to transmit a tension force of 300 pounds or more during operation of the apparatus. Similarly, outer tube assembly 60, which holds staple holding assembly 40 stationary with respect to actuator assembly 14 during tissue clamping, may be required to transmit a compression force of 50 pounds or more, and inner tube assembly 70, which supplies the force for driving the staples and the knife, may be required to transmit a compression force of 200 pounds or more. These forces are transmitted through the flexible portions 64, 74 of the tube assemblies 60, 70 without causing the flexible portions 64, 74 to revert to their straight condition by means of the structure of segments 600, 700 and the cooperation of these segments with flexible band 80. We turn now to that structure and cooperation.

Looking at band 80 first, when that band is curved and is transmitting longitudinal tension force, a resultant force is produced which acts on the band 80 along its length and seeks to straighten the band 80. The direction of this resultant force is normal to the longitudinal axis of the band 80 and towards the center of curvature of the band. The magnitude of the resultant force depends upon the local curvature of band 80 and will be different at points on the band having different local curvatures. As a first approximation, band 80 can be considered to behave like a thin flexible cable or catenary for which a longitudinal tension force T produces a resultant force F which varies as the second derivative of the shape $\Psi(x)$ of the cable:

$$F = T \frac{d^2 \Psi(x)}{dx^2}.$$

The compression members 60 and 70, and in particular their flexible portions 64 and 74, behave in essentially the same manner as band 80 when these members are curved and are transmitting longitudinal compression force. Thus members 60, 70 each also produce a resultant force normal to their respective longitudinal axes and having a magnitude which varies with the local curvature of the member 60 or 70 (i.e., to a first approximation, with the second derivative of the shape of the member). This compression-generated resultant force, however, points in the opposite direction to the tension-generated force; that is, the compression-generated resultant force points out from the center of curvature of the compression member. This means that for equal tension and compression forces and for the same local curvatures, the tension member, i.e., band 80, and the compression members, i.e., tube assembly 60 and tube assembly 70, produce equal and opposite resultant forces. Accordingly, by balancing these forces against each other, the tension member and the compression members can hold each other in equilibrium so that neither member will revert to its straight condition, and both will transmit longitudinal force. As we now discuss, segments 600, 700, band 80 and the resultant force transmitting members 704a and 704b (FIG. 11) are constructed and arranged to achieve this result of balanced resultant forces.

Referring to FIGS. 7 through 14, a first embodiment of shaft assembly 16 using segments 600, 700, which make contact through cylindrically shaped projections 602a-d, 702a-d, is illustrated. As shown particularly in FIG. 11, the overall construction of the flexible portion 13 of shaft assembly 16 includes flexible band 80 whose longitudinal axis lies in the median plane of the shaft assembly; resultant force transmitting members 704a, 704b, which respectively lie above and below band 80; washer-shaped segments 700 of inner tube assembly 70;

elastic sheath 710; washer-shaped segments 600 of outer tube assembly 60; and outer elastic sheath 610.

Considering segments 600, 700 first, these segments are constructed to rotate by pivoting against each other as shaft assembly 16 is deformed into a curve. The pivoting is permitted by the spaces between the bodies of adjacent segments 600, 700 provided by projections 602a–d, 702a–d (see FIG. 12).

The projections themselves make contact with the projections on adjacent segments so as to define a line of contact between each two adjacent segments. This line contact is illustrated in FIG. 21, where it can be seen that segment 600n contacts segment 600n+1 along line 34n. Similarly, segment 700n contacts segment 700n+1 along the same line, although, as discussed below, the lines of contacts for the segments 600 and segments 700 can be longitudinally off-set from each other. As shown in FIG. 12, the line contact between segments is maintained throughout the range of rotation of one segment with respect to its neighboring segment.

The lines of contact 34 together define a geometric surface 36. Band 80, or more particularly the longitudinal axis 88 of band 80, is designed to lie in this surface 36 (FIG. 21). The local curvatures of band 80, which is transmitting longitudinal tension force, and of the curve of contact points of both tube assemblies 60 and 70, which are transmitting longitudinal compression forces, are therefore the same. Accordingly, as discussed above, for equal tension and compression forces the resultant forces normal to the longitudinal axis of shaft assembly 16 produced by band 80 and tube assembly 60 or tube assembly 70 will be equal and opposite.

The lines of contact for segments 600 and for segments 700 need not coincide as shown in FIG. 21, provided they lie in the same geometric surface 36. This latter condition will produce equal local curvatures, which in turn will produce equal resultant forces for equal longitudinal forces. Accordingly, segments 600 and segments 700 need not be longitudinally aligned, nor do they have to have equal longitudinal dimensions, that is, there can be more segments in tube assembly 60 than in tube assembly 70, or vice versa.

Recessed portions 720 (FIG. 9) of segments 700 maintain alignment between projections 702a–d and are sized to allow relative longitudinal motion between the band and tube assembly 70 during the operations of tissue clamping and driving of the staples and the knife assembly.

Figure 13:
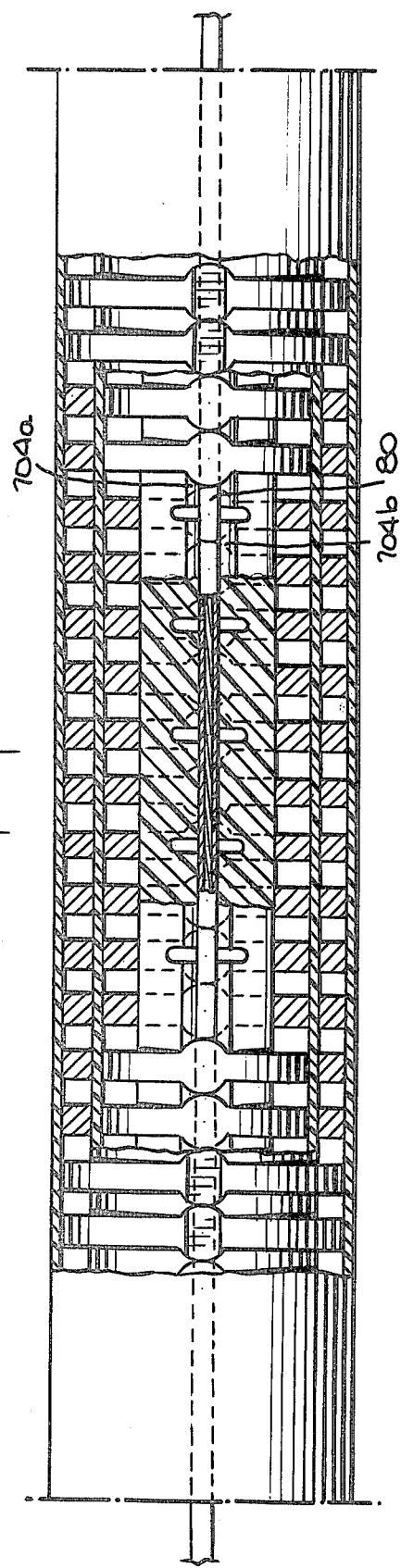
Figure 14:
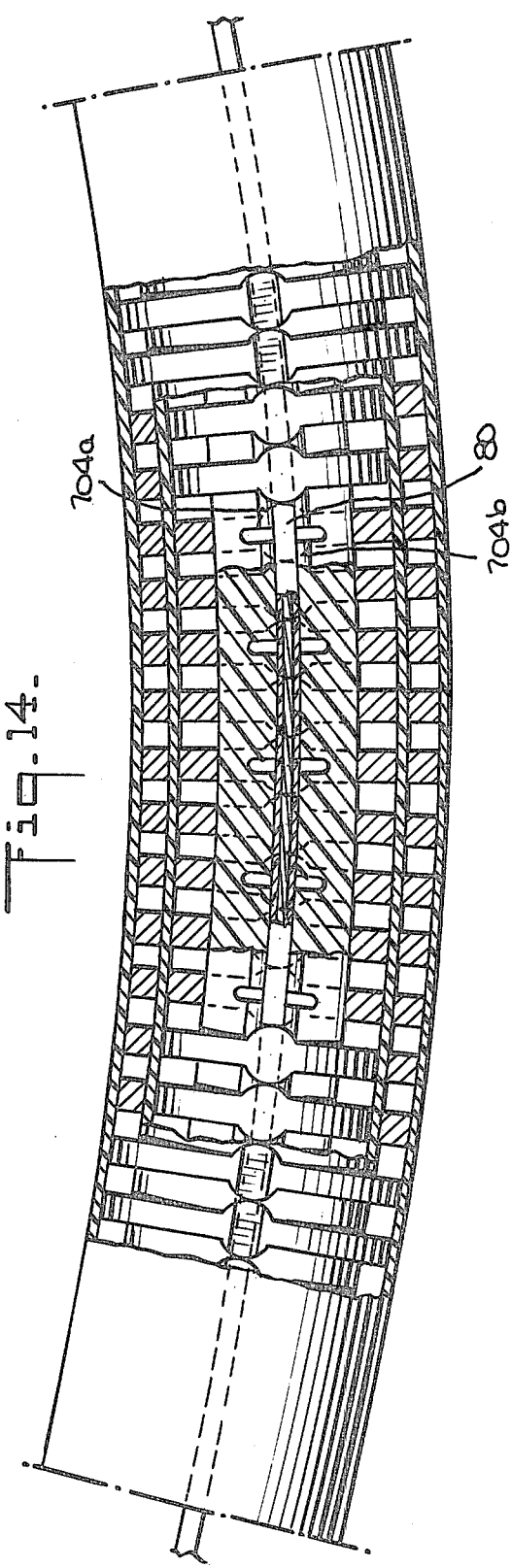

The elements for holding band 80 in surface 36 are resultant force transmitting members 704a and 704b (FIG. 11). These members fit in the space between band 80 and the inner surface of segments 700 of inner tube assembly 70 (FIG. 10) and make contact with that band and those segments along the entire length of the flexible portion 74 of inner tube assembly 70. Members 704a and 704b are made of a flexible, low friction plastic material such as nylon or Teflon and are provided with slots 706 (FIG. 11) to increase their flexibility. The low friction allows relative longitudinal motion between band 80 and members 704a and 704b during the clamping of tissue and between these members and shaft assembly 70 during the driving of staples 50 and cutting knife 52. The flexibility, as shown in FIGS. 13 and 14, allows members 704a and 704b to maintain contact with band 80 and segments 700 as shaft assembly 16 is deformed into a curve.

During the transmission of longitudinal forces, onlly one of members 704a and 704b serves as the means for transmitting resultant force, specifically, the member 704a or 704b on the concave side of band 80. Thus, in FIG. 14, when tube assembly 70 is transmitting longitudinal force, band 80 produces an upwardly directed resultant force and segments 700 produce downwardly directed resultant forces. Member 704a, being between segments 700 and band 80, serves as the means for balancing these resultant forces. Of course, when shaft assembly 16 has a curvature opposite to that shown in FIG. 14, that is, downward, then member 704b, rather than member 704a, serves as the means for transmitting resultant force.

Although the principal function of band 80 is to transmit longitudinal tension forces, occasionally this band 80 transmits minor longitudinal compression force, e.g., to move anvil assembly 20 away from stable holding assembly 40 after the tissue has been stapled. In this case, the member 704a or 704b on the convex, rather than the concave, side of band 80 (member 704b in FIG. 14) transmits the resultant force produced by band 80. The balance of resultant forces is analogous to that described above; however, the magnitude of the forces is in the range of only a few pounds, and the effect on the mechanics of the instrument is inconsequential. The unbalanced compression force in band 80 in this case is an order of magnitude less than the frictional forces between the band 80 and segments 700. The compression in band 80 necessary to overcome this friction is balanced by tension in the sheaths 610, 710, which prevents the segments 600, 700 from separating. There is no similar balance for the compression force due to contact of the anvil with tissue as the anvil is moved away from the staple holding assembly 40. As noted, however, the total compression load on the band 80 during movement of the anvil assembly 20 away from the staple holding assembly 40 after stapling is only a few pounds, and band 80 cannot readily buckle in this lightly loaded compression state, because it is confined on all sides.

Surrounding segments 700 is elastic sheath 710 (FIG. 11). This sheath is made of a lightweight plastic material and is provided with a low friction outer surface, as, for example, by coating the outer surface with Teflon (i.e., polytetrafluoroethylene). The sheath 710 serves two primary functions. First, the sheath transmits the compression-produced result force of tissue clamping from outer tube assembly 60 to segments 700. This force then passes through segments 700 to force transmitting members 704a and 704b and finally to band 80, where it is balanced by the complementary resultant force of tissue clamping produced by tension in band 80. Thus, sheath 710 provides part of the link between the equal and opposite forces normal to the longitudinal axis of shaft assembly 16 produced by the longitudinal compression and tension forces transmitted by tube assembly 60 and band 80, respectively, during tissue clamping.

Second, sheath 710, by means of its low friction outer surface, allows shaft assembly 70 to move distally relative to shaft assembly 60 without undue resistance during the driving of staples 50 and cutting knife 52. In addition, as discussed above, sheath 710 contributes to the confinement of band 80 when that band is moving anvil assembly 20 away from staple holding assembly 40.

Disposed about sheath 710 are segments 600 of tube assembly 60. As discussed above, segments 600 have essentially the same construction and arrangement in the instrument as segments 700. In particular, segments 600 include cylindrical projections 602a–d which make line contact with the projections on neighboring segments, with the lines lying in a surface which includes the longitudinal axis of band 80. Segments 600 serve to transmit longitudinal compression force from actuator assembly 14 to stapling assembly 12 during the clamping of tissue, with the resultant force normal to the longitudinal axis of shaft assembly 16 produced by the longitudinal compression force being transmitted to band 80 by sheath 710, segments 700 and force transmitting member 704a or 704b.

Surrounding segments 600 is elastic sheath 610 which serves as the outer surface of the flexible portion 13 of shaft assembly 16. Sheath 610 is made of a lightweight plastic material and is provided with a smooth outer surface which will not snag tissue during positioning of the instrument relative to the tissue to be stapled. Sheath 610 is fastened at its proximal end to body 100 and at its distal end to staple holder 42. The sheath 610 is preferably assembled with small initial longitudinal tension, to hold segments 600 in contact with each other with a small compressive preload. Sheath 610 has two internal ribs 611 that cooperate with notches 601 in each segment 600 to maintain alignment between projections 602a-d. Ribs 611 also align sheath 610 with body 100 and with staple holder 42. As with sheath 710, sheath 610 adds a limited degree of rigidity to the flexible portion 13 of shaft assembly 16, which is desirable in handling the instrument.

FIGS. 15 through 20 illustrate two alternate embodiments for the segments 600, 700 of tube assemblies 60, 70. In FIGS. 15 through 17, the segments 630, 730 have flat rear surfaces 632, 732 and front surfaces which have two bevelled portions 634, 734, and 636, 736 that slope away from the flat surface 632 or 732 of the next forward segment 630 or 730. Bevelled portions 634 and 636 meet, and bevelled portions 734 and 736 meet, along lines 738 that serve as the lines of contact between adjacent segments about which the segments pivot with respect to each other as shaft assembly 16 is deformed into a curve.

In FIGS. 18 through 20, the segments 640, 740 have flat rear surfaces 642 (not shown, but similar to 742), 742 and front surfaces which have flat portions 644 (not shown, but similar to 744), 744 and bevelled portions 646, 746 that slope away from the flat rear surface 642, 742 of the next forward segment 640, 740. The flat portions 644, 744 and the bevelled portions 646, 746 meet along lines 748 that, like lines 738, serve as the lines of contact between adjacent segments about which the segments pivot with respect to each other as shaft assembly 16 is deformed into a curve. Because segments 640, 740 are bevelled only above the median plane of the instrument, this embodiment of shaft assembly 16 can only be deformed in that direction, as indicated in FIG. 19.

In both alternative embodiments, as in the first embodiment (FIGS. 7-14), band 80 lies in the surface defined by the family of lines 738 or 748. As discussed above, the local curvatures of band 80 and of either tube assembly 60 or tube assembly 70 are therefore essentially equal, and essentially equal and opposite resultant forces normal to the longitudinal axis of shaft assembly 16 are produced for equal longitudinal tension and compression forces in band 80 and in tube assembly 60 or tube assembly 70 or both. Likewise, as in the first embodiment, the resultant forces are balanced by means of members 704a, 704b, which contact band 80 and the inner surface of segments 730 (740), and, in the case of segments 630 (640), by means of sheath 710 which surrounds segments 730 (740) and transmits force from segments 630 (640) to elements 730 (740) and thus to members 704a, 704b.

The segments of all three embodiments have the common characteristic of easy fabrication, so that they are inexpensive to produce. Various materials can be used for the segments, such as hard plastics, aluminum or steel, provided the selected materials can withstand, without significant deformation, the compression forces encountered during operation of the instrument. These forces can be as high as 300 pounds during the driving of staples 50 and knife 52.

The remaining components of flexible shaft assembly 16, including band 80, resultant force transmitting members 704a, 704b, and sheaths 610 and 710, are also relatively easy to construct and can be made of inexpensive and lightweight materials. In this way, the complete instrument can economically be made disposable after a single use, if desired.

Although in each of the three embodiments illustrated, the same type of segment is used for both tube assemblies 60 and 70, it is to be understood that the two tube assemblies need not use identically configured segments. Thus, segments 700, having cylindrical projections, can be used for inner tube assembly 70 in combination with doubly bevelled segments 630 for outer tube assembly 60, or vice versa. Other flexible structures and segment configurations can also be used, provided the tension member and the compression members produce essentially equal and opposite resultant forces for equal longitudinal forces.

Considering now the overall operation of the apparatus, the initial position of anvil assembly 20 is approximately the substantially fully retracted position shown in FIG. 1, and the initial position of tube assembly 70 is the proximal position shown in FIGS. 2 and 3. In this condition stapling assembly 12 is passed through organ section 18a until anvil assembly 20 is adjacent the severed end of that organ section. Wing nut 150 is then rotated to cause rod 160 and flexible band 80 to extend rod 30 from stable holding assembly 40 so that pursestring suture 19a can be drawn around rod 30 between assemblies 20 and 40 as shown in FIG. 3. Anvil assembly 20 is inserted in the severed end of organ section 18b, and purse-string suture 19b is drawn around rod 30 as also shown in FIG. 3.

When both organ sections have been secured to rod 30 as described above, wing nut 150 is rotated to cause rod 160 and flexible band 80 to retract rod 30 in the proximal direction. During this portion of the operation of the apparatus, flexible band 80 is typically under relatively low tension due to the force required to pull the two organ sections together. As anvil assembly 20 moves toward staple holding assembly 40, indicator marks 163 on the proximal end of rod 160 move toward the proximal end of wing nut 150.

As shown in FIGS. 4 and 5, when anvil assembly 20 is sufficiently close to staple holding assembly 40 that staples 50 can be properly clinched by the anvil, indicator marks 163 become visible in slots 154a and 154b near the proximal end of wing nut 150. This is a visual indication to the operator that the instrument is ready to staple the tissue.

When indicator marks 163 are visible in slots 155a and 154b and it is desired to staple the tissue, safety collar 130 is rotated by means of tabs 134a and 134b to release handles 120a and 120b from engagement by wings 132a and 132b. The tissue is then stapled by squeezing handles 120a and 120b together to the broken line positions shown in FIG. 4. This causes tube assembly 70 to translate in the distal direction as a result of the engagement of handle projections 126a and 126b in tube slots 71a and 71b, respectively.

Distal translation of tube assembly 70 causes corresponding distal translation of staple and knife pusher assembly 44. This in turn drives staples 50 and knife 52 as shown in FIG. 6. The legs of staples 50 pass through the tissue and are clinched by contact with staple anvil 22 to secure the two organ sections together with an annular array of staples. Knife 52 cuts through the excess tissue inside the annular staple array to clear the lumen between the connected organ sections. The stapling procedure is now complete and handles 120a and 120b can be released so that they will return to their initial outer position.

The stapled tissue is released from the apparatus by operating wing nut 150 again to separate anvil assembly 20 from staple holding assembly 40. The instrument is then removed by withdrawing it via organ section 18a. The excess tissue cut away by knife 52 remains secured to rod 30 by sutures 19a and 19b and is therefore removed with the instrument.

It will be understood that the foregoing is only illustrative of the principles of the invention, and that various modifications can be made by those skilled in the art without departing from the scope and spirit of the invention. For example, the particular actuator assembly configuration shown is not critical, and other actuator arrangements can be used if desired. One possible alternative is an acuator in which the handles for driving tube 70 are substantially perpendicular to the longitudinal axis of the instrument. Such actuators are well-known for instruments of this type, as shown, for example in the abovementioned Conta et al. U.S. Pat. No. 4,304,236.

We claim:

1. A longitudinally flexible shaft assembly for connecting the actuator of a surgical stapler to the remotely located stapling assembly of the stapler and for simultaneously transmitting longitudinal tension and compression forces between the actuator and the stapling assembly, the shaft assembly retaining its longitudinal flexibility while transmitting the tension and compression forces, the shaft assembly comprising:
   a longitudinally flexible tension member for transmitting longitudinal tension force along a first geometrical surface parallel to the longitudinal axis of the shaft assembly, the tension member being flexible perpendicular to the first surface;
   longitudinally flexible compression means for transmitting longitudinal compression force along a second geometrical surface substantially coincident with the first surface, the compression means being flexible perpendicular to the second surface;
   a longitudinally flexible longitudinal element for transmitting longitudinal force along a third geometrical surface substantially coincident with the first surface, the longitudinal element being flexible perpendicular to the third surface; and
   longitudinally flexible force-transmitting means for transmitting resultant forces perpendicular to the first, second, and third surfaces for keeping the first, second, and third surfaces substantially coincident while allowing relative longitudinal motion between the tension member, the compression means, and the longitudinal element.

2. Surgical stapling apparatus comprising:
   a stapling assembly comprising two parts between which tissue is stapled;
   an actuator assembly remote from the stapling assembly for controlling the stapling assembly; and
   a longitudinal shaft assembly according to claim 1 for connecting the stapling assembly to the actuator assembly; and wherein the forces transmitted between the actuator and the stapling assembly include forces for controlling the stapling assembly.

3. The apparatus of claim 2, wherein the force-transmitting means substantially prevents friction between the tension member and the compression means during relative longitudinal motion of the tension member and the compression means.

4. The apparatus of claim 2, wherein one of the two parts of the stapling assembly is an anvil assembly, and the other of the two parts is a staple holding assembly containing a plurality of surgical staples and including (a) anvil support means for supporting the anvil assembly for motion relative to the staple holding assembly to allow the tissue to be stapled to be clamped between the staple holding assembly and the anvil assembly and (b) pusher means for driving the staples from the staple holding assembly through the clamped tissue and against the anvil assembly; and wherein the actuator assembly includes a first actuator for controlling the anvil support means and a second actuator for controlling the pusher means;
   the tension member being for transmitting longitudinal tension force from the first actuator to the anvil support means to move the anvil assembly toward the staple holding assembly to clamp the tissue and to resist the force of the staples being driven through the tissue and against the anvil assembly;
   the compression means including a first longitudinally flexible compression member for transmitting longitudinal compression force from the second actuator to the pusher means to cause the pusher means to drive the staples;
   the longitudinally flexible longitudinal element including a second longitudinally flexible compression member for transmitting longitudinal compression force between the actuator assembly and the staple holding assembly to resist the tissue clamping force exerted by the anvil assembly;
   the first compression member and the tension member producing in the flexible shaft assembly essentially equal and opposite resultant forces normal to the longitudinal axis of the flexible shaft assembly when transmitting equal longitudinal forces, and the second compression member and the tension member producing in the flexible shaft assembly essentially equal and opposite resultant forces normal to the longitudinal axis of the flexible shaft assembly when transmitting equal longitudinal forces; and
   the force-transmitting means allowing relative longitudinal motion of the tension member, the first compression member, and the second compression member.

5. The apparatus of claim 4, wherein the apparatus is for joining two hollow organ sections with an annular array of staples between the organ sections and surrounding an organ lumen, wherein the anvil support means comprises a rod extending between the staple holding assembly and the anvil assembly, and wherein the surgical staples are contained in the staple holding assembly in an annular array surrounding the rod.

6. The apparatus of claim 5, wherein the staple holding assembly further includes an annular knife mounted on the pusher means and surrounding the rod for cooperating with the anvil assembly to cut through the tissue inside the annular array of staples as the staples are being driven.

7. A longitudinally flexible shaft assembly for connecting the actuator of a surgical stapler to the remotely located stapling assembly of the stapler and for simultaneously transmitting longitudinal tension and compression forces between the actuator and the stapling assembly, the shaft assembly retaining its longitudinal flexibility while transmitting the tension and compression forces, the shaft assembly comprising:
- a longitudinally flexible tension member for transmitting longitudinal tension force along a first geometrical surface parallel to the longitudinal axis of the shaft assembly, the tension member being flexible perpendicular to the first surface;
- longitudinally flexible compression means for transmitting longitudinal compression force along a second geometrical surface substantially coincident with the first surface, the compression means being flexible perpendicular to the second surface and comprising a plurality of substantially non-compressible elements disposed in series along the length of the shaft assembly, each non-compressible element being in longitudinal contact with the adjacent non-compressible elements, the contacting surfaces of adjacent non-compressible elements being so contoured that contact between each two adjacent non-compressible elements occurs at least along a respective line which lies in the second surface;
- a longitudinally flexible longitudinal element for transmitting longitudinal force along a third geometrical surface substantially coincident with the first surface, the longitudinal element being flexible perpendicular to the third surface; and
- longitudinally flexible force-transmitting means for transmitting resultant forces perpendicular to the first, second, and third surfaces for keeping the first, second, and third surfaces substantially coincident while allowing relative longitudinal motion between the tension member, the compression means, and the longitudinal element.

8. The apparatus of claim 7, wherein an elastic sheath surrounds the non-compressible elements.

9. The apparatus of claim 7, wherein each of the non-compressible elements has a longitudinal aperture, the tension member passing through the apertures.

10. The apparatus of claim 9, wherein each of the non-compressible elements includes a guide means which slidably receives the tension member.

11. The apparatus of claim 7 or 8, wherein each of the non-compressible elements has first and second contacting surfaces, the first contacting surface being for contacting the second contacting surface of an adjacent non-compressible element; and each first contacting surface being essentially flat, each second contacting surface having an essentially flat portion and a bevelled portion sloping away from the flat contacting surface of the adjacent non-compressible element, and contact between contacting surfaces of adjacent non-compressible elements occurring at the junction on the second contacting surface of the flat portion with the bevelled portion.

12. The apparatus of claim 7 or 9, wherein each of the non-compressible elements has first and second contacting surfaces, the first contacting surface being for contacting the second contacting surface of an adjacent non-compressible element; and each first contacting surface being essentially flat, each second contacting surface having two bevelled portions each of which slopes away from the flat surface of the adjacent non-compressible element, and contact between adjacent non-compressible elements occurring at the junction on the second contacting surface of the two bevelled portions.

13. The apparatus of claim 7 or 9, wherein each of the contacting surfaces of each of the non-compressible elements includes a cylindrical projection at which the surfaces of adjacent non-compressible elements make contact.

14. The apparatus of claim 9, wherein the force-transmitting means comprises a longitudinal member whose coefficient of friction with the tension member is sufficiently low to permit easy manual sliding of the tension member relative to the compression means.

15. The apparatus of claim 7 or 9, wherein the tension member is a band of rectangular cross section having its major cross sectional dimension lying substantially in the first surface.

16. Apparatus for connecting first and second sections of hollow body organ by means of an annular array of surgical staples surrounding a lumen which communicates with the interiors of both organ sections, said apparatus comprising:
- a first hollow tube assembly having a longitunally flexible section, the distal portion of the first tube assembly being adapted for insertion through the interior of the first of the organ sections;
- a staple holding assembly mounted on the distal end of the first tube assembly and adapted for insertion through the first organ section, the staple holding assembly containing an annular array of surgical staples ejectable from the distal end of the staple holding assembly and including staple ejection means;
- an anvil assembly adapted for insertion in the second of the organ sections;
- means associated with the staple holding assembly for mounting the anvil assembly for longitudinal reciprocal motion relative to the distal end of the staple holding assembly;
- an actuator assembly mounted on the proximal end of the first tube assembly;
- a longitudinally flexible member disposed in the first tube assembly for longitudinal reciprocal motion relative to the first tube assembly for operatively connecting the means for mounting the anvil assembly to the actuator assembly for transmitting a longitudinal tension force from the actuator assembly to the means for mounting the anvil assembly to move the anvil assembly toward the distal end of the staple holding assembly to clamp the first and second organ sections together between the anvil assembly and the distal end of the staple holding assembly, and to hold the anvil assembly adjacent the distal end of the staple holding assembly so that the staples ejected from the staple holding assembly are clinched by the anvil assembly; and a second hollow tube assembly concentric with and disposed in the first tube assembly for longitudinal motion relative to the first tube assembly for transmitting a longitudinal compression force from the actuator assembly to the staple ejection means for ejecting the staples from the staple holding assembly, the second tube assembly having a longitudinally flexible section within the longitudinally flexible section of the first tube assembly.

17. Apparatus for connecting first and second sections of hollow body organ by means of an annular array of surgical staples surrounding a lumen which communicates with the interiors of both organ sections, said apparatus comprising:

a first hollow tube assembly having a longitudinally flexible section, the distal portion of the first tube assembly being adapted for insertion through the interior of the first of the organ sections;

a staple holding assembly mounted on the distal end of the first tube assembly and adapted for insertion through the first organ section, the staple holding assembly containing an annular array of surgical staples ejectable from the distal end of the staple holding assembly and including staple ejection means;

an anvil assembly adapted for insertion in the second of the organ sections;

means associated with the staple holding assembly for mounting the anvil assembly for longitudinal reciprocal motion relative to the distal end of the staple holding assembly;

an actuator assembly mounted on the proximal end of the first tube assembly;

a longitudinally flexible member disposed in the first tube assembly for longitudinal reciprocal motion relative to the first tube assembly for operatively connecting the means for mounting the anvil assembly to the actuator assembly for transmitting a longitudinal tension force from the actuator assembly to the means for mounting the anvil assembly to move the anvil assembly toward the distal end of the staple holding assembly to clamp the first and second organ sections together between the anvil assembly and the distal end of the staple holding assembly, and to hold the anvil assembly adjacent the distal end of the staple holding assembly so that the staples ejected from the staple holding assembly are clinched by the anvil assembly; and a second hollow tube assembly concentric with and disposed in the first tube assembly for longitudinal motion relative to the first tube assembly for transmitting a longitudinal compression force from the actuator assembly to the staple ejection means for ejecting the staples from the staple holding assembly, the second tube assembly having a longitudinally flexible section within the longitudinally flexible section of the first tube assembly;

wherein the flexible sections of the first and second hollow tube assemblies each comprises a plurality of segments in a longitudinal series which make line contact with each other, the line contacts for the segments of each of the tubes lying in a geometric surface, and further comprising means for maintaining the longitudinal axis of the portion of the flexible tension transmitting member corresponding to the flexible sections of the first and second tubes in the geometric surface.

18. The apparatus of claim 17, wherein each of the segments of the flexible sections of both the first and second hollow tubes has a first, essentially flat surface and a second surface for contacting the first surface of an adjacent segment, the second surface having an essentially flat portion and a bevelled portion which slopes away from the first surface of an adjacent segment, the line contact between adjacent segments being coincident with the junction of the flat and bevelled portions.

19. The apparatus of claim 17, wherein each of the segments of the flexible sections of both the first and second hollow tubes has a first, essentially flat surface and a second surface for contacting the first surface of an adjacent segment, the second surface having two bevelled portions each of which slopes away from the first surface of an adjacent segment, the line contact between adjacent segments being coincident with the junction of the two bevelled portions.

20. The apparatus of claim 17, wherein each of the segments of the flexible sections of both the first and second hollow tubes includes a cylindrical projection making a line contact with an adjacent segment.

21. The apparatus of claim 17, wherein the maintaining means comprises a first elongated member of low friction material disposed between the flexible tension transmitting member and the inner surface of the flexible section of the second tube, and a second elongated member of low friction material disposed between the flexible sections of the first and second tubes.

* * * * *

UNITED STATES PATENT AND TRADEMARK OFFICE
CERTIFICATE OF CORRECTION

PATENT NO. : 4,473,077

DATED : September 25, 1984

INVENTOR(S) : Douglas G. Noiles et al.

It is certified that error appears in the above-identified patent and that said Letters Patent is hereby corrected as shown below:

Col. 4, line 37, "necessary" should be --desirable--

Col. 9, lines 43-48, "Recessed portions 720 (FIG. 9) of segments 700 maintain alignment between projections 702a-d and are sized to allow relative longitudinal motion between the band and tube assembly 70 during the operations of tissue clamping and driving of the staples and knife assembly."

should be
--To help maintain band 80 in surface 36 and to establish the initial alignment between the band 80 and tube assembly 70, segments 700 can include recessed portions 720 (Figure 9). These portions journal the band 80 and are sized to allow relative longitudinal motion between the band and tube assembly 70 during the operations of tissue clamping and driving of the staples and the knife assembly.--

UNITED STATES PATENT AND TRADEMARK OFFICE
CERTIFICATE OF CORRECTION

PATENT NO. : 4,473,077                              Page 2 of 2

DATED      : September 25, 1984

INVENTOR(S) : Douglas G. Noiles et al.

It is certified that error appears in the above-identified patent and that said Letters Patent is hereby corrected as shown below:

Col. 9, line 49, After "The" insert --main--

Col. 9, line 49, After "36" insert --, however,--

Col. 9, line 67, "onlly" should be --only--

Col. 12, line 65, "155a" should be --154a--

Col. 13, line 1, "sequeezing" should be --squeezing--

Signed and Sealed this

Twenty-fifth Day of June 1985

[SEAL]

Attest:

DONALD J. QUIGG

Attesting Officer     Acting Commissioner of Patents and Trademarks